United States Patent [19]

Nakahata et al.

[11] Patent Number: 5,668,104
[45] Date of Patent: Sep. 16, 1997

US005668104A

[54] HEMATOPOIETIC STEM CELL GROWTH-PROMOTING COMPOSITIONS CONTAINING A FIBROBLAST-DERIVED FRAGMENT OF FIBRONECTIN AND A GROWTH FACTOR, AND METHODS EMPLOYING THEM IN VITRO OR IN VIVO

[75] Inventors: Tatsutoshi Nakahata, Matsumoto; Genji Kawano; Tetsuo Sudo, both of Kamakura; Katsuaki Kojima, Yokohama, all of Japan

[73] Assignee: Toray Industries, Inc., Tokyo, Japan

[21] Appl. No.: 142,449

[22] PCT Filed: Mar. 31, 1993

[86] PCT No.: PCT/JP93/00404

§ 371 Date: Apr. 26, 1994

§ 102(e) Date: Apr. 26, 1994

[87] PCT Pub. No.: WO93/20228

PCT Pub. Date: Oct. 14, 1993

[30] Foreign Application Priority Data

Mar. 31, 1992 [JP] Japan ................... 4-076894

[51] Int. Cl.$^6$ ............... C07K 14/47; A61K 38/17; A61K 38/39
[52] U.S. Cl. ............... 514/2; 530/351; 530/380; 530/381; 424/85.1; 435/69.1
[58] Field of Search ................... 530/380, 381, 530/350, 351, 395; 435/69.1, 240.2, 252.3, 254.11; 514/2, 8; 424/85.1

[56] References Cited

FOREIGN PATENT DOCUMENTS 1261398 10/1989 Japan.
3123799 5/1991 Japan.
91/17765 11/1991 WIPO.

OTHER PUBLICATIONS

Kornblihtt, A.R., et al. (1985) *EMBO J*, 4(7): 1755–59.
Chang, Z.-L., et al (1993) *J. Leukocyte Biol.* 53: 79–85.
Weinstein, et al. "Dual role of fibronectin in hematopoietic differentiation", Biol. Abs. 87: 55451, 1989.
Weinstein, et al. "Dual role of fibronectin in hematopoietic differentiation", Blood 73: 111–116, 1989.

*Primary Examiner*—Stephen G. Walsh
*Assistant Examiner*—David L. Fitzgerald
*Attorney, Agent, or Firm*—White & Case

[57] ABSTRACT

An 18 kDa protein, denominated FDF-3, has been isolated from cultures of human fibroblasts and has been found to potentiate the growth- and differentiation-promoting activities of certain cytokines toward hematopoietic progenitor cells. The amino acid sequence of the FDF-3 protein, shown in SEQ ID NO: 14, corresponds to the sequence of a C-terminal domain of human fibronectin. The protein is useful in combination with IL-3, G-CSF, GM-CSF, or SCF (stem cell factor) in the expansion of hematopoietic cell populations in vitro or in therapeutic methods to promote recovery from leukopenia or myelosuppresion in vivo.

11 Claims, 3 Drawing Sheets

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 20 amino acids
( B ) TYPE: amino acid
( D ) TOPOLOGY: linear ( i i ) MOLECULE TYPE: protein ( v ) FRAGMENT TYPE: N-terminal ( x i ) SEQUENCE DESCRIPTION: SEQ ID NO:1:

Asn Gln Pro Thr Asp Asp Ser Cys Phe Asp Pro Tyr Thr Val Ser His
1               5                   10                  15
Tyr Ala Val Gly
        20

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear     ( i i ) MOLECULE TYPE: protein     ( v ) FRAGMENT TYPE: internal     ( x i ) SEQUENCE DESCRIPTION: SEQ ID NO:2:

```
Thr Tyr His Val Gly Glu Gln Trp Gln Lys
1               5                   10
```

( 2 ) INFORMATION FOR SEQ ID NO:3:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: Other nucleic acid (Synthesized DNA)

( i v ) ANTI-SENSE: NO

( x i ) SEQUENCE DESCRIPTION: SEQ ID NO:3:

AACCAACCTA CGGATGACTC            20

( 2 ) INFORMATION FOR SEQ ID NO:4:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: Other nucleic acid (Synthesized DNA)

( i v ) ANTI-SENSE: YES

( x i ) SEQUENCE DESCRIPTION: SEQ ID NO:4:

TTAGTCTCGG GAATCTTCTC            20

( 2 ) INFORMATION FOR SEQ ID NO:5:

( i ) SEQUENCE CHARACTERISTICS:
        ( A ) LENGTH: 567 base pairs
        ( B ) TYPE: nucleic acid
        ( C ) STRANDEDNESS: double
        ( D ) TOPOLOGY: linear     ( i i ) MOLECULE TYPE: cDNA to mRNA     ( i x ) FEATURE:
        ( A ) NAME/KEY: CDS     ( x i ) SEQUENCE DESCRIPTION: SEQ ID NO:5:

```
AAC CAA CCT ACG GAT GAC TCG TGC TTT GAC CCC TAC ACA GTT TCC CAT      48
Asn Gln Pro Thr Asp Asp Ser Cys Phe Asp Pro Tyr Thr Val Ser His
1               5                   10                  15

TAT GCC GTT GGA GAT GAG TGG GAA CGA ATG TCT GAA TCA GGC TTT AAA      96
Tyr Ala Val Gly Asp Glu Trp Glu Arg Met Ser Glu Ser Gly Phe Lys
        20                  25                  30

CTG TTG TGC CAG TGC TTA GGC TTT GGA AGT GGT CAT TTC AGA TGT GAT     144
Leu Leu Cys Gln Cys Leu Gly Phe Gly Ser Gly His Phe Arg Cys Asp
35                  40                  45

TCA TCT AGA TGG TGC CAT GAC AAT GGT GTG AAC TAC AAG ATT GGA GAG     192
Ser Ser Arg Trp Cys His Asp Asn Gly Val Asn Tyr Lys Ile Gly Glu
```

```
                50                           55                           60
AAG  TGG  GAC  CGT  CAG  GGA  GAA  AAT  GGC  CAG  ATG  ATG  AGC  TGC  ACA  TGT      240
Lys  Trp  Asp  Arg  Gln  Gly  Glu  Asn  Gly  Gln  Met  Met  Ser  Cys  Thr  Cys
 65                      70                       75                        80

CTT  GGG  AAC  GGA  AAA  GGA  GAA  TTC  AAG  TGT  GAC  CCT  CAT  GAG  GCA  ACG      288
Leu  Gly  Asn  Gly  Lys  Gly  Glu  Phe  Lys  Cys  Asp  Pro  His  Glu  Ala  Thr
 85                      90                       95

TGT  TAC  GAT  GAT  GGG  AAG  ACA  TAC  CAC  GTA  GGA  GAA  CAG  TGG  CAG  AAG      336
Cys  Tyr  Asp  Asp  Gly  Lys  Thr  Tyr  His  Val  Gly  Glu  Gln  Trp  Gln  Lys
         100                     105                     110

GAA  TAT  CTC  GGT  GCC  ATT  TGC  TCC  TGC  ACA  TGC  TTT  GGA  GGC  CAG  CGG      384
Glu  Tyr  Leu  Gly  Ala  Ile  Cys  Ser  Cys  Thr  Cys  Phe  Gly  Gly  Gln  Arg
115                     120                     125

GGC  TGG  CGC  TGT  GAC  AAC  TGC  CGC  AGA  CCT  GGG  GGT  GAA  CCC  AGT  CCC      432
Gly  Trp  Arg  Cys  Asp  Asn  Cys  Arg  Arg  Pro  Gly  Gly  Glu  Pro  Ser  Pro
     130                     135                     140

GAA  GGC  ACT  ACT  GGC  CAG  TCC  TAC  AAC  CAG  TAT  TCT  CAG  AGA  TAC  CAT      480
Glu  Gly  Thr  Thr  Gly  Gln  Ser  Tyr  Asn  Gln  Tyr  Ser  Gln  Arg  Tyr  His
145                     150                     155                     160

CAG  AGA  ACA  AAC  ACT  AAT  GTT  AAT  TGC  CCA  ATT  GAG  TGC  TTC  ATG  CCT      528
Gln  Arg  Thr  Asn  Thr  Asn  Val  Asn  Cys  Pro  Ile  Glu  Cys  Phe  Met  Pro
165                     170                     175

TTA  GAT  GTA  CAG  GCT  GAC  AGA  GAA  GAT  TCC  CGA  GAG  TAA                    567
Leu  Asp  Val  Gln  Ala  Asp  Arg  Glu  Asp  Ser  Arg  Glu  ***
          180                     185
```

( 2 ) INFORMATION FOR SEQ ID NO:6:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear     ( x i ) SEQUENCE DESCRIPTION: SEQ ID NO:6:

TTAATTAACA TTAGTGTTTG TTCT                24

( 2 ) INFORMATION FOR SEQ ID NO:7:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear     ( i i ) MOLECULE TYPE: Other nucleic acid (Synthesized DNA)

( x i ) SEQUENCE DESCRIPTION: SEQ ID NO:7:

TTAAACATTA GTGTTTGTTC TCTG                24

( 2 ) INFORMATION FOR SEQ ID NO:8:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear     ( i i ) MOLECULE TYPE: Other nucleic acid (Synthesized DNA)

( x i ) SEQUENCE DESCRIPTION: SEQ ID NO:8:

TTAATTAGTG TTTGTTCTCT GATG                24

( 2 ) INFORMATION FOR SEQ ID NO:9:

( i ) SEQUENCE CHARACTERISTICS:
  ( A ) LENGTH: 24 bases
  ( B ) TYPE: nucleic acid
  ( C ) STRANDEDNESS: single
  ( D ) TOPOLOGY: linear ( i i ) MOLECULE TYPE: Other nucleic acid (Synthesized DNA)

( x i ) SEQUENCE DESCRIPTION: SEQ ID NO:9:

TTAAGTGTTT GTTCTCTGAT GGTA  24

( 2 ) INFORMATION FOR SEQ ID NO:10:

( i ) SEQUENCE CHARACTERISTICS:
  ( A ) LENGTH: 24 bases
  ( B ) TYPE: nucleic acid
  ( C ) STRANDEDNESS: single
  ( D ) TOPOLOGY: linear ( i i ) MOLECULE TYPE: Other nucleic acid (Synthesized DNA)

( x i ) SEQUENCE DESCRIPTION: SEQ ID NO:10:

TTAGTTTGTT CTCTGATGGT ATCT  24

( 2 ) INFORMATION FOR SEQ ID NO:11:

( i ) SEQUENCE CHARACTERISTICS:
  ( A ) LENGTH: 24 bases
  ( B ) TYPE: nucleic acid
  ( C ) STRANDEDNESS: single
  ( D ) TOPOLOGY: linear ( i i ) MOLECULE TYPE: Other nucleic acid (Synthesized DNA)

( x i ) SEQUENCE DESCRIPTION: SEQ ID NO:11:

TTATGTTCTC TGATGGTATC TCTG  24

( 2 ) INFORMATION FOR SEQ ID NO:12:

( i ) SEQUENCE CHARACTERISTICS:
  ( A ) LENGTH: 24
  ( B ) TYPE: nucleic acid
  ( C ) STRANDEDNESS: single
  ( D ) TOPOLOGY: linear ( i i ) MOLECULE TYPE: Other nucleic acid (Synthesized DNA)

( x i ) SEQUENCE DESCRIPTION: SEQ ID NO:12:

TTATCTCTGA TGGTATCTCT GAGA  24

( 2 ) INFORMATION FOR SEQ ID NO:13:

( i ) SEQUENCE CHARACTERISTICS:
  ( A ) LENGTH: 4
  ( B ) TYPE: amino acid
  ( C ) STRANDEDNESS: single
  ( D ) TOPOLOGY: linear ( i i ) MOLECULE TYPE: protein ( i x ) SEQUENCE DESCRIPTION: SEQ ID NO:13:

Arg Gly Asp Ser  4
 1

( 2 ) INFORMATION FOR SEQ ID NO:14:

( i ) SEQUENCE CHARACTERISTICS:
  ( A ) LENGTH: 188 amino acids
  ( B ) TYPE: amino acid
  ( D ) TOPOLOGY: linear ( i i ) MOLECULE TYPE: protein ( x i ) SEQUENCE DESCRIPTION: SEQ ID NO:14:

```
Asn Gln Pro Thr Asp Asp Ser Cys Phe Asp Pro Tyr Thr Val Ser His
 1               5                  10                  15

Tyr Ala Val Gly Asp Glu Trp Glu Arg Met Ser Glu Ser Gly Phe Lys
     20                  25                  30

Leu Leu Cys Gln Cys Leu Gly Phe Gly Ser Gly His Phe Arg Cys Asp
 35                  40                      45

Ser Ser Arg Trp Cys His Asp Asn Gly Val Asn Tyr Lys Ile Gly Glu
     50              55                  60

Lys Trp Asp Arg Gln Gly Glu Asn Gly Gln Met Met Ser Cys Thr Cys
 65                  70                  75                  80

Leu Gly Asn Gly Lys Gly Glu Phe Lys Cys Asp Pro His Glu Ala Thr
 85                  90                  95

Cys Tyr Asp Asp Gly Lys Thr Tyr His Val Gly Glu Gln Trp Gln Lys
     100             105                 110

Glu Tyr Leu Gly Ala Ile Cys Ser Cys Thr Cys Phe Gly Gly Gln Arg
 115                 120                 125

Gly Trp Arg Cys Asp Asn Cys Arg Arg Pro Gly Gly Glu Pro Ser Pro
     130             135                 140

Glu Gly Thr Thr Gly Gln Ser Tyr Asn Gln Tyr Ser Gln Arg Tyr His
 145                 150                 155                 160

Gln Arg Thr Asn Thr Asn Val Asn Cys Pro Ile Glu Cys Phe Met Pro
 165                 170                 175

Leu Asp Val Gln Ala Asp Arg Glu Asp Ser Arg Glu
 180                 185
```

HEMATOPOIETIC STEM CELL GROWTH-PROMOTING COMPOSITIONS CONTAINING A FIBROBLAST-DERIVED FRAGMENT OF FIBRONECTIN AND A GROWTH FACTOR, AND METHODS EMPLOYING THEM IN VITRO OR IN VIVO

FIELD OF THE INVENTION

The present invention relates to a new physiologically active protein having growth activity for undifferentiated hematopoietic stem cells and a hematopoietic stem cell growth agent containing said protein as an active ingredient.

BACKGROUND OF THE INVENTION

It has been recently found that in the process of differentiation from the undifferentiated hematopoietic stems cell to mature blood cells, a number of hematopoietic factors mutually interact at various levels to form a complicated hematopoietic network system. In addition, most of these hematopoietic factors are gene-cloned and at present time, some of the hematopoietic factors are mass-produced by means of genetic recombination technologies and their clinical applications have been developed. On the other hand, the undifferentiated hematopoietic stem cells exhibit a feature having capacity of self-renewal (proliferation) but growth factors that could act on the undifferentiated hematopoietic stem cells in the bone marrow have not been sufficiently clarified.

It is known that for proliferation of the hematopoietic stem cells in the bone marrow and differentiation to the mature cells, the bone marrow stromal cells play a central role and it is suggested that the humoral factors which the stromal cells secrete and/or cell-cell interactions take part in the proliferation of undifferentiated hematopoietic stem cells.

For example, it is known that a bone marrow stromal cell MC3T3-G2/PA-6(PA-6) established from the calvaria of a C57B⅙ neonatal mouse supports proliferation of murine pluripotent hematopoietic stem cells [Kodama H. et al: J. Cell Physiol., 112, 89 (1982)].

Recently, a ligand for c-kit protein on the surface of the hematopoietic stem cells is given attention as a factor taking part in the proliferation of the stem cell and researches for clarifying the true function have been extensively conducted and as the result, three groups have succeeded in the gene cloning to report SCF [stem cell factor; K. M. Zsebo et al: Cell, 63, 195–201 (1990)], MGF [mast cell growth factor; D. E. Williams et al: Cell, 63, 167–174 (1990) and KL [c-kit ligand; Huang et al: Cell, 63, 225–233 (1990)].

At present time, by using c-kit ligand mass-produced by means of a genetic recombination technology, analysis of the function has been developed and it has been clarified from researches by now that this factor supports proliferation of the hematopoietic stem cells having been differentiated in some extent [Hayashi et at.: Int. J. Hematology, Supple. No. 1, p198 (1990)]. Therefore, it is considered that besides this protein, another factor acting on the undifferentiated stem cell should exist in the bone marrow.

A hematopoietic factor supporting the proliferation of undifferentiated stem cells will be a useful medicine which is used as a remedy for suppression of the bone marrow, for example, recovery of suppression of the bone marrow in chemotherapy for cancer or bone marrow transplantation or a remedy for bone marrow malfunction such as aplastic anemia and myelodysplasia syndrome and furthermore, used for bone marrow transplantation as an in vitro growth agent for the peripheral blood stem cells and the bone marrow stem cell.

The purpose of the present invention is to provide a new protein having growth activity for undifferentiated hematopoietic stem cells and the hematopoietic stem cells growth agent containing said protein as an active ingredient and used for curing for suppression of the bone marrow, or curing for incompetence of the bone marrow or an in vitro proliferation for the peripheral blood stem cells and the bone marrow stem cells.

As it is known that the bone marrow stromal cells are constituted of the fibroblast/the preadipocyte, the endothelial cell and the macrophage and produces such hematopoietic factors as interleukin 1, interleukin 6, interleukin 7, interleukin 8, interleukin 11, c-kit ligand, LIF (leukemia inhibitory factor), GM-CSF, G-CSF and M-CSF, the present inventors thought that a growth factor to the undifferentiated hematopoietic stem cells exists in the human fibroblast cell-conditioned medium.

It is known that the hematopoietic cells obtained from the bone marrow of a mouse in which a large amount of 5-fluorouracil (5FU) had been administered are called pre spleen colony forming &Its (pre CFU-S) and are the undifferentiated hematopoietic stem cells with high capacity of self-renewal.

The present inventors have extensively studied to aim separation of a new physiologically active protein from a culture medium of the fibroblast by using growth activity to the 5-FU resistant murinebone marrow cells as a target. As the result, a new physiologically active protein having a growth activity for the undifferentiated hematopoietic stem cells has been isolated to complete the present invention.

DISCLOSURE OF THE INVENTION

The present invention relates to a new physiologically active protein which has an activity supporting proliferation of the undifferentiated hematopoietic stem cells and has a molecular weight of 18,000±2,000 and has an N-terminal amino acid sequence shown in the SEQ ID NO:1 in the Sequence Listing. In addition, the physiologically active protein of the present invention has an amino acid composition shown in Table 1, infra. In addition, the physiologically active protein of the present invention is a protein consisting of the amino acid sequence from the first to the 162nd amino acid, a protein consisting of the amino acid sequence from the first to the 163rd amino acid, a protein consisting of the amino acid sequence from the first to the 164th amino acid, a protein consisting of the amino acid sequence from the first to the 165th amino acid, a protein consisting of the amino acid sequence from the first to the 166th amino acid, a protein consisting of the amino acid sequence from the first to the 167th amino acid, a protein consisting of the amino acid sequence from the first to the 168th amino acid or a protein consisting of the amino acid sequence from the first to the 188th amino acid shown in SEQ ID NO: 14 in the Sequence Listing.

BRIEF DESCRIPTION OF DRAWINGS

FIGS. 2-A and 2-B depict a method for construction of an expressing vector pSRαFN14.

BEST MODE FOR CARRYING OUT THE INVENTION

The physiologically active protein of the present invention (abbreviated as FDF-3 hereinafter) belongs to a new hematopoietic factor judging from its N-terminal amino acid sequence and amino acid composition. In addition, from the amino acid sequence analysis, it was suggested that the physiologically active protein of the present invention was a part of fibronectin. It is known that fibronectin enhances the effect of erythropoietin increasing the proliferation of erythrocytic cells (Weinsteon, R., et at., Blood. 73, 11 (1989)) and as this enhancement is inhibited with a tetrapeptide Arg-Gly-Asp-Ser (RGDS) SEQ ID NO: 13 in the Sequence Listing, it was indicated that a part wherein the RGDS sequence existed in fibronectin was responsible for this enhancement. However, as no RGDS sequence exists in the physiologically active protein of the present invention, it belongs to a new hematopoietic factor distinct from the domains containing RGDS sequence.

In addition, the present inventors confirmed that said physiologically active protein supported proliferation of the hematopoietic stem cells in an evaluation system using murine bone marrow cells and have completed a new hematopoietic stem cell growth agent wherein said physiologically active protein is an active ingredient.

As the material for obtaining the new physiologically active protein of the present invention, a culture medium for the human fibroblast is usually used. Namely, the human fibroblast is cultured in a medium containing a bovine serum and after it reaches a definite number of cells, it is exchanged with a serum-free medium to produce said protein. The obtained cultured medium is purified by using a silica chromatography, a heparin affinity chromatography, an anion exchange chromatography a metal chelating affinity chromatography, a gel filtration chromatography, a hydroxyapatite chromatography etc., to obtain a pure substance. Otherwise, a fragment containing the amino acid sequence of the present invention can be obtained by digesting fibronectin with such a protease as thermolysin and/or trypsin and the above described method.

In addition, the physiologically active substance (FDF-3) of the present invention can be obtained constantly and largely by means of a recombinant DNA technology. Namely, a cDNA containing a nucleotide sequence encoding the polypeptide of the human FDF-3 can be obtained from the cDNA library prepared from human fibroblast mRNA by using an oligonucleotide synthesized based on the amino acid of FDF-3 as a probe. In addition, as FDF-3 of the present invention is a fragment of a part of fibronection, cDNA encoding FDF-3 can be obtained by the following procedure; denaturation of DNA, annealing and extention of two kinds of primers, synthesized by means of DNA synthesizer, specific to the 5' and 3' end of the part of fibronectin is nucleotide sequences corresponding to the polypeptide of FDF-3, in the presence of a DNA polymerase such as Taq DNA polymerase using a DNA thermal cycler, for example, of Perkin-Elmer Cetus Co., Ltd. The cDNA thus obtained is integrated in various expression vectors and transformed bodies transformed with said recombinant expression vectors are cultured transformants to obtain a recombinant human FDF-3 from the cultured substances.

As a vector used for expressing FDF-3, there exists a DNA fragment encoding a part of or the whole amino acid sequence of the FDF-3 polypeptide under the control of a promoter. Various promotors are reported as the promoter and such a promoter as a promoter for SV40 which can express in mammalian cells is preferable in the present invention. At the downstream of this promoter, there exists a signal-like sequence existing in a gene of a secretory protein and in addition, followed by, the DNA fragment of the FDF-3 gene in accordance with the direction of transcription. In this case, the part of structural gene used for signal sequence may be contained. As the signal sequence of the secretory protein that of, a cytokine such as interleukin-6 can be utilized. In addition, it is necessary that a polyadenylation signal exists at the downstream of said FDF-3 gene. As the polyadenylation signal, for example, that of SV40DNA, β-globin gene or metallothionein can be used.

An animal cell, for example, COS- 1 cell or CHO cell, can be transformed by said vector. For introducing an expression vector into the mammalian cell, a calcium phosphate coprecipitation method, a DEAE dextran method, an electroporation method, a microinjection method etc., can be used.

The transformed mammalian cell is cultured as described above and the cultured product can be purified by means of various chromatographies.

Details of physicochemical properties and biological properties of the physiologically active protein of the present invention obtained by said method are described hereinbelow.

(1) Molecular weight: 18,000±2,000 [SDS-polyacrylamide gel electrophoresis method (Laemmli U. K.: Nature, 227,680–685 (1970)]

(2) N-terminal amino acid sequence (20 residues): It is shown on the sequence number 1 of the Sequence Listing.

(3) A partial amino acid sequence (10 residues): It is shown on the sequence number 2 of the Sequence Listing.

(4) The whole amino acid sequence It is shown on the sequence number 14 of the Sequence Listing.

(5) Amino acid composition It is shown on Table 1.

(6) Biological activity: It exhibits growth activity in combination with IL-3, with G-CSF, with stem cell factor or with both IL-3 and G-CSF, on bone marrow cells of 5-FU treated mice. In addition it exhibits growth activity in combination with GM-CSF on human umbilical cord monocyte.

The physiologically active protein of the present invention (FDF-3) exhibits growth activity to the undifferentiated hematopoietic stem cells and is useful as an effective hematopoietic stem cell growth agent for curing for suppression of the bone marrow, (for example, after using an anticancer drug and bone marrow transplantation), as an effective hematopoietic stem cell growth agent for curing for bone marrow malfunction (for example, aplastic anemia and myelodysplasia syndrome) or as an effective hematopoietic stem cell growth agent for proliferation in vitro for the peripheral blood stem cells and the bone marrow stem cells.

Namely, as FDF-3 of the present invention works especially with IL-3 and stimulates formation of a blast cell colonies which is the undifferentiated blood cells, it is useful as a hematopoietic stem cell growth agent and in addition, as FDF-3 works synergistically with SCF, G-CSF, GM-CSF and IL-3 and it remarkably stimulates formation of colonies of bone marrow cells of a mammal such as a mouse treated with 5-fluorouracil, it is used as an enhancing agent for recovery of the bone marrow for curing bone marrow malfunction and suppression of the bone marrow which occur by administering a chemical remedy (5-FU). This is effective not only for recovery of the bone marrow after administering a chemical remedy but also for recovery of the bone marrow after a radiotherapy.

In addition, as FDF-3 of the present invention stimulates formation of a megakaryocyte colonies (CFU-Meg) and it is thought that it increases production of the platelet released from the megakaryocyte, it is useful as a platelet growth agent. In addition, as FDF-3 works synergistically with SCF, G-SCF, GM-SCF and IL-3 and increases leucocytes such as neutrophils, it is effective as a remedy for leukopenia in mammals.

When the physiologically active protein of the present invention is used to said applications of the present invention, it can be administered orally or parentally as itself or as a pharmaceutical composition Wherein it is mixed with vehicles, excipients etc., which themselves are well known and pharmacologically allowed.

As the forms of the drug for oral application, tablets, pills, capsules, granules, medicated syrups, emulsions, suspensions etc., are practically used. These forms of the drug are manufactured by means of a well known method itself and vehicles or excipients which are usually used in the pharmaceutical field are contained. For example, as the vehicles and excipients for tablets, lactose, starch, cane sugar, magnesium stearate etc., are cited.

As the forms of the drug for parenteral application, for example, ointments, injection, wet packs, coating agents, inhalations, suppositories, percutaneously absorptive agents etc., are used. The injections are prepared by a method being itself well known, for example, by dissolving, suspending or emulsifying the protein of the present invention in an aseptic aqueous or oleosus liquid being usually used for parenteral agents. As the water solutions for injection, physiological saline solution, glucose solution etc., are used and as the oleosus liquid, sesame oil, soybean oil etc., are used and solubilizers may be respectively used in combination. The suppositories used for intestinal administration are prepared by a method being well known themselves, for example, by mixing the protein of the present invention with a usual base for suppositories and molding the mixture.

Effective dose and the number of administration of the protein of the present invention depend on forms of the administration, age and weight of the patients, characteristics or seriousness of the symptom and 0.01–100 mg, preferably 0.1–10 mg of the protein can be usually administered by one time or by being divided into several times per an adult.

EXAMPLES

The invention is further illustrated by the following examples but the invention is not limited to these examples.

Example 1

Culture of human fibroblast

Using a 30 L culture tank, human fibroblast was cultured in MEM supplemented with 10% FBS and 0.3% microcarrier beads (cytodex 1; manufactured by Pharmacia Co., Ltd) at 37° C. for 5 days with stirring. After the cell growth reached confluent, the medium was replaced with a fresh MEM medium and protein production was induced by the addition of poly I/C (10 μg/ml). The culture was continued at 37° C. for 4 days and then 20 liters of Culture Supernatant were recovered.

Ammonium sulfate was added to make 60% saturation and after the obtained precipitation was dissolved in 20 mM Tris hydrochloric acid buffer solution (pH 8.0), the solution was dialyzed against the same buffer solution and was desalted.

This solution was adsorbed on a heparin Sepharose column (0.5 L carrier: manufactured by Pharmacia Co., Ltd.) equilibrated with 20 mM Tris hydrochloric acid buffer solution (pH 8.0) and then, the column was washed with the buffer solution used for equilibration. The unadsorbed fraction and the washed fraction were mixed and were adsorbed on a DEAE cellulofine column (0.5 L carrier: manufactured by Seikagaku Co., Ltd.) equilibrated with 20 mM Tris hydrochloric acid buffer solution (pH 8.0) and the column was washed with the buffer solution used for equilibration. Then, the protein was eluted by a linear concentration gradient of NaCl from 0M to 1M.

250 ml of the obtained active fraction were adsorbed on Zn-chelated Sepharose column (30 ml carrier: manufactured by Pharmacia Co., Ltd.) equilibrated with 20 mM Tris hydrochloric acid buffer solution (pH 8.0) containing 0.5M NaCl and the column was washed with the buffer solution used for equilibration. After protein impurities were removed with 20 mM Tris hydrochloric acid buffer solution (pH 8.0) containing 1M $NH_4Cl$, adsorbed proteins were eluted with 0–50 mM imidazole (0.5M NaCl-containing 20 mM Tris hydrochloric acid buffer solution, pH 8.0). 20 ml of the obtained active fraction were gel-filtered by using a Sephacryl S100HR column (1 L carrier: manufactured by Pharmacia Co., Ltd.) equilibrated with 0.5M NaCl-containing 20 mM iris hydrochloric acid buffer solution (pH 8.0). 20 ml active fraction were adsorbed on Zn chelated Sepharose column equilibrated with 20M Tris hydrochloric acid buffer solution (pH 8.0) containing 0.5M Nacl and after they were washed with the buffer solution used for equilibration, adsorbed proteins were eluted with 0–50 mM imidazole (0.5M NaCl containing 20 mM Tris hydrochloric acid buffer solution, pH 8.0).

Active peak fraction was applied to SDS-PAGE under non-reducing condition and a single band with a molecular weight of 18,000–2,000 was exhibited.

Example 2

N-terminal amino acid sequence and amino acid composition

The purified protein obtained by Example 1 was analyzed by means of an amino acid sequencer (Applied Biosystems 477A Protein Sequencer); as a result, the sequence of 20 amino acids at N-terminal was determined as shown in the sequence number 1 in the Sequence Listing. In addition, after this purified protein was digested with endopeptidase, the peptide was fractionareal by means of a reverse phase high performance liquid chromatography (Vydac $C_{18}$) and the amino acid sequence of the obtained fragment was analyzed by means of said amino acid sequencer. The amino acid sequence of this fragment was found to be the sequence number 2 of the Sequence Listing.

4 μg/25 ul of this purified protein were incorporated with 25 μl concentrated hydrochloric acid containing 0.4% thioglycotic acid and after hydrolysis was performed under vacuum sealing at 110° C. for 22 hours, hydrochloric acid was dried under reduced pressure and then, this was dissolved in distilled water and subjected to amino acid analysis using an amino acid analyser (Hitachi Type 835 Amino Acid Analyser). The result was shown in Table 1.

TABLE 1

| Amino acid | mol % | Amino acid | mol % |
|---|---|---|---|
| Asp + Asn | 11.50 | Met | 1.91 |
| Thr | 4.71 | Ile | 1.72 |
| Ser | 6.36 | Leu | 4.08 |
| Glu + Gln | 12.67 | Tyr | 4.10 |

TABLE 1-continued

| Amino acid | mol % | Amino acid | mol % |
|---|---|---|---|
| Pro | 4.08 | Phe | 3.98 |
| Gly | 14.01 | Lys | 4.78 |
| Ala | 3.14 | His | 3.64 |
| ½Cys | 8.10 | Trp | 2.24 |
| Val | 3.43 | Arg | 5.54 |

Example 3

Analysis of FDF-3 by using anti-human fibronectin monoclonal antibody

Figure 1:
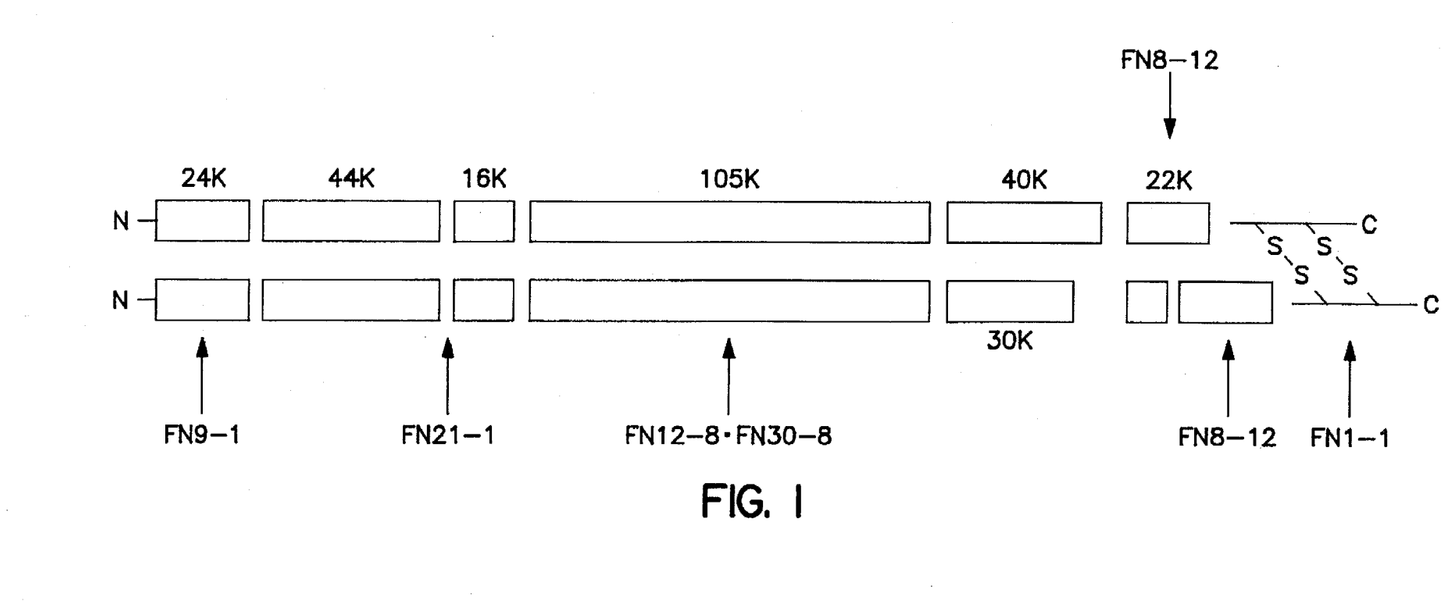
FIG. 1 shows a model figure of a limited digested fragments of fibronectin with thermolysin and domains recognized by each monoclonal antibody.

As it was clarified from the N-terminal amino acid sequence, the partial amino acid sequence and the amino acid composition in Example 2 that FDF-3 was the fragment involved C-terminal region of fibronectin, analysis of FDF-3 was performed by using anti-human fibronectin monoclonal antibody. It was known that human fibronectin was fragmented into several pieces by limiting digestion using thermolysin and trypsin [Sekiguchi, K. et al.: J. Biol. Chem., 260, 5105 (1985)] and anti-fibronectin monoclonal antibody FN8-12 recognized a fragment with a molecular weight of 22,000 and FN-1-1 recognized a dimer having disulfide bond with a molecular weight of 6,000 obtained by limiting digestion in the similar way. In Table 1, a model figure of fragments of fibronectin obtained by limiting digestion with thermolysin and domains recognized by each monoclonal antibody was shown [Ichihara-Tanaka, K., et al., J. Biol. Chem., 265, 401 (1990); Katayama, M., et al., Clin. Chem., 37,466 (1991)].

FDF-3 obtained in Example 1 and human fibronectin (Iwaki Co., Ltd.) were treated by SDS-polyacrylamide electrophoresis (4–20%) under reduction condition. Thereafter, immobilization of proteins on a nitrocellulose membrane by electrophoretic transfer from a gel was performed by Western blot technique, and after the membrane was blocked with skim milk, FN8-12 or FN-1-1 (both were purchased from Takara Shuzo Co., Ltd.) was added and incubated for 1 hour. After washing, anti-mouse Ig antibody labeled with horseradish peroxidase was added and incubated for 1 hour and after washing, proteins reacting with a monoclonal antibody were detected by an ECL system (purchased from Areasham Co., Ltd.). As the result, it was found that FN8-12 but not FN1-1 recognize FDF-3. It was suggested from the result described that above FDF-3 did not have a disulfide bond on its C-terminal.

Example 4

Measurement of growth activity on hematopoietic stem cells by using murine bone marrow cells 150 mg/Kg 5-fluorouracil was injected intravenously to a BDF1 female mice and after 48 hours, bone marrow cells were prepared from the thigh bone.

Culture thereof was performed by means of a methylcellulose method which is a modified method of Iscove's et at. $5 \times 10^4$ bone marrow cells were added to a serum-free medium having the following composition and the total volume of the culture was made into 1 ml.

The medium contained α-medium, 0.9% methylcellulose, 1% crystallized deionized bovine serum albumin, 300 µg/ml Fe-saturated human transferrin, 160 µg/ml soybean lecithin (manufactured by Sigma Co., Ltd.), 96 ug/ml cholesterol (manufactured by Nakarai Co., Ltd.), $10^{-4}$M 2-mercaptoethanol and samples or various hematopoietic factors were dispensed into each 35 mm Lux culture dishes. Each hematopoietic factor was added at the following concentration: rmuIL-3 (Cosmo Bio): 200 u/ml, rhuG-CSF (Cosmo Bio): 20 u/ml.

The culture was performed in an incubator at 37° C., with 5% $CO_2$ and 100% humidity.

After incubation for 12 days colonies were observed under an inverted microscope and the number of colonies was counted. The results were shown in Table 2.

TABLE 2

Hematopoietic stem cell growth activity of FDF-3 on 5FU-treated murine bone marrow cell Formation of colonies/5 × 10⁴ 5FU-resistant bone marrow cells

| Growth factor | CFU-G | CFU-GMM | CFU-GM | CFU-Meg | Macrophage | Total |
|---|---|---|---|---|---|---|
| No addition | 0 | 0 | 0 | 0 | 0 | 0 |
| FDF-3 | 0 | 0 | 0 | 0 | 0 | 0 |
| +IL-3 | 5 | 3 | 16 | 3 | 1 | 28 |
| +G-CSF | 5 | 0 | 2 | 0 | 0 | 7 |
| IL-3 | 3 | 0 | 8 | 1 | 2 | 14 |
| G-CSF | 0 | 0 | 0 | 0 | 0 | 0 |

FDF-3; 900 ng/ml
IL-3; 100 U/ml
G-CSF; 50 ng/ml

Example 5

Using a mouse stem cell factor (mSCF) instead of G-CSF of Example 4, the same measurements as those of Example 4 were performed. The results are shown in Table 3.

TABLE 3

Hematopoietic stem cell growth activity of FDF-3 on 5FU-treated murine bone marrow cell Formation of colonies/5 × 10⁴ 5FU-resistant bone marrow cells

| Growth factor | CFU-G | CFU-GM | Macrophage | CFU-Meg | CFU-GMM | Blast | Total |
|---|---|---|---|---|---|---|---|
| No addition | 0 | 0 | 0 | 0 | 0 | 0 | 0 |
| FDF-3 | 0 | 0 | 0 | 0 | 0 | 0 | 0 |
| FDF-3 + IL-3 | 2.7 ± 0.5 | 11.0 ± 4.5 | 1.7 ± 1.2 | 0.3 ± 0.5 | 3.0 ± 1.6 | 1.3 ± 0.5 | 20.0 ± 4.3 |

TABLE 3-continued

| | Hematopoietic stem cell growth activity of FDF-3 on 5FU-treated murine bone marrow cell | | | | | | |
|---|---|---|---|---|---|---|---|
| | Formation of colonies/$5 \times 10^4$ 5FU-resistant bone marrow cells | | | | | | |
| Growth factor | CFU-G | CFU-GM | Macrophage | CFU-Meg | CFU-GMM | Blast | Total |
| FDF-3 + SCF | 5.0 ± 2.2 | 12.0 ± 1.7 | 0 | 0 | 0 | 1.7 ± 1.7 | 19.0 ± 2.2 |
| IL-3 | 1.7 ± 0.9 | 2.7 ± 0.9 | 1.3 ± 1.2 | 0.3 ± 0.5 | 0.7 ± 0.5 | 0.7 ± 0.5 | 7.3 ± 1.7 |
| SCF | 1.0 ± 0.8 | 5.3 ± 0.5 | 0 | 0 | 0 | 1.3 ± 0.9 | 7.7 ± 2.1 |

FDF-3; 200 ng/ml
IL-3; 100 U/ml
SCF; 100 ng/ml

Example 6

Measurements of growth activities of blood cells by using human umbilical cord blood monocytes Monocytes were separated from a human umbilical cord blood and using the medium described in Example 4 and adding a sample or various hematopoietic factors, culture was performed in an incubator at 37° C., with 5 % $CO_2$, 5% $N_2$ and 100 % humidity. Colonies on the 14th days and on the 21st days were observed under an inverted microscope to count the number of colonies. The results were shown in Table 4. The concentrations, of the sample and the hematopoietic factors were as follows. FDF-3:1 µg/ml, human fibronectin (Iwaki): 10 µg/ml, human GM-CSF (Cosmo Bio): 50 ng/ml.

(2) Cloning of FDF-3cDNA

As it was suggested from Examples 2 and 3 that FDF-3 was a fragment of fibronectin, a sense primer was synthesized based on the nucleotide sequence of fibronectin [Kornblihtt, A. et al., Nucleic Acids Res. 12, 5853 (1984)] being the same as the N-terminal amino acid sequence of FDF-3 and an anti-sense primer was synthesized based on C-terminal base sequence of fibronectin by means of a DNA synthesizer. The nucleotide sequences of the primers were shown below.

Sense primer: 5'AACCAACCTACGGATGACTC3' (The sequence number 3 in the Sequence Listing)

Anti-sense primer: 5'TTAGTCTCGGGAATCTTCTC3' (The sequence number 4 in the Sequence Listing)

cDNA was synthesized from 1 µg poly(A)RNA obtained by described in (1) according to the Gubler's et al

TABLE 4

| | Hematopoiesis by FDF-3 on human umbilical cord blood monocytes | | | | | | | |
|---|---|---|---|---|---|---|---|---|
| Growth factor | Formation of colonies (on the 14th days) | | | | Formation of colonies (on the 21st days) | | | |
| | CFU-G | CFU-GM | Macrophage | Total | CFU-G | CFU-GM | Macrophage | Total |
| No addition | 0 | 0 | 0 | 0 | 0 | 0 | 0 | 0 |
| Fibronectin | 0 | 0 | 0 | 0 | 0 | 0 | 0 | 0 |
| FDF-3 | 0.3 ± 0.5 | 0 | 0 | 0.3 ± 0.5 | 0 | 0 | 0 | 0 |
| hGM-CSF | 0 | 0 | 0 | 0 | 0.3 ± 0.5 | 0 | 0 | 0.3 ± 0.5 |
| FDF-3 + hGM-CSF | 0 | 2.3 ± 0.9 | 1.0 ± 1.0 | 3.3 ± 1.7 | 1.0 ± 0 | 3.0 ± 0.8 | 2.0 ± 0.8 | 6.0 ± 1.4 |
| Fibronectin + hGM-CSF | 0 | 0 | 0 | 0 | 0 | 0 | 0 | 0 |

FDF-3; 1 µg/ml
Fibronectin; 10 µg/ml
hGM-CSF; 50 ng/ml

Example 7

Preparation of a recombinant FDF-3:

(1) Preparation of human normal fibroblast mRNA

RNA was prepared from a human normal fibroblast by means of the lithium chloride/urea method [Auffrey et al., Eur. J. Biochem. 107, 303 (1980)]. The obtained RNA was dissolved in 10 mM Tris heating hydrochloric acid buffer (pH 7.5) containing 1 mM EDTA (referred to as TE hereinafter) and after heating the solution at 70° C. for 5 minutes, the same mount of TE containing 1M LiCl was incorporated therein. The RNA solution was added to an oligo dT cellulose column equilibrated with TE containing 0.5M LiCl and after it was washed with the same buffer, adsorbed poly (A) RNA was eluted with 2 m MEDTA solution (pH 7.5) containing 0.01% SDS.

[Gubler, V., et at., Gene., 25, 236 (1987)]. 1/20 of the synthesized cDNA and each 20 pmol of above-mentioned two kinds of primers were taken in a 0.5 ml micro-centrifugal tube and 20 mM Tris hydrochloric acid buffer (pH 8.3), 1.5 mM $MgCl_2$, 25 mM KCl, 100 µg/ml gelatin, 50 µM each dNTP, were added so as to make 4 units TaqDNA polymerase and to make the total amount 100 gl. Reactions of 35 cycles under a condition wherein the denaturation condition of DNA was at 94° C. for 1 minute and the annealing condition of the primer was at 58° C. for 2 minutes and the extension condition of the primer was at. 72° C. for 3 minutes were performed by using a DNA thermal cycler of Perkin-Elmer Cetus Co., Ltd. The reaction product was subjected to a 1% agarose gel electrophoresis and DNA fragment of 570 bp was prepared according to the conventional method (Molecular Cloning. Cold Spring Harbor Laboratory, New York, 1982).

(3) Preparation of an FDF-3 expression vector

Figure 2A:
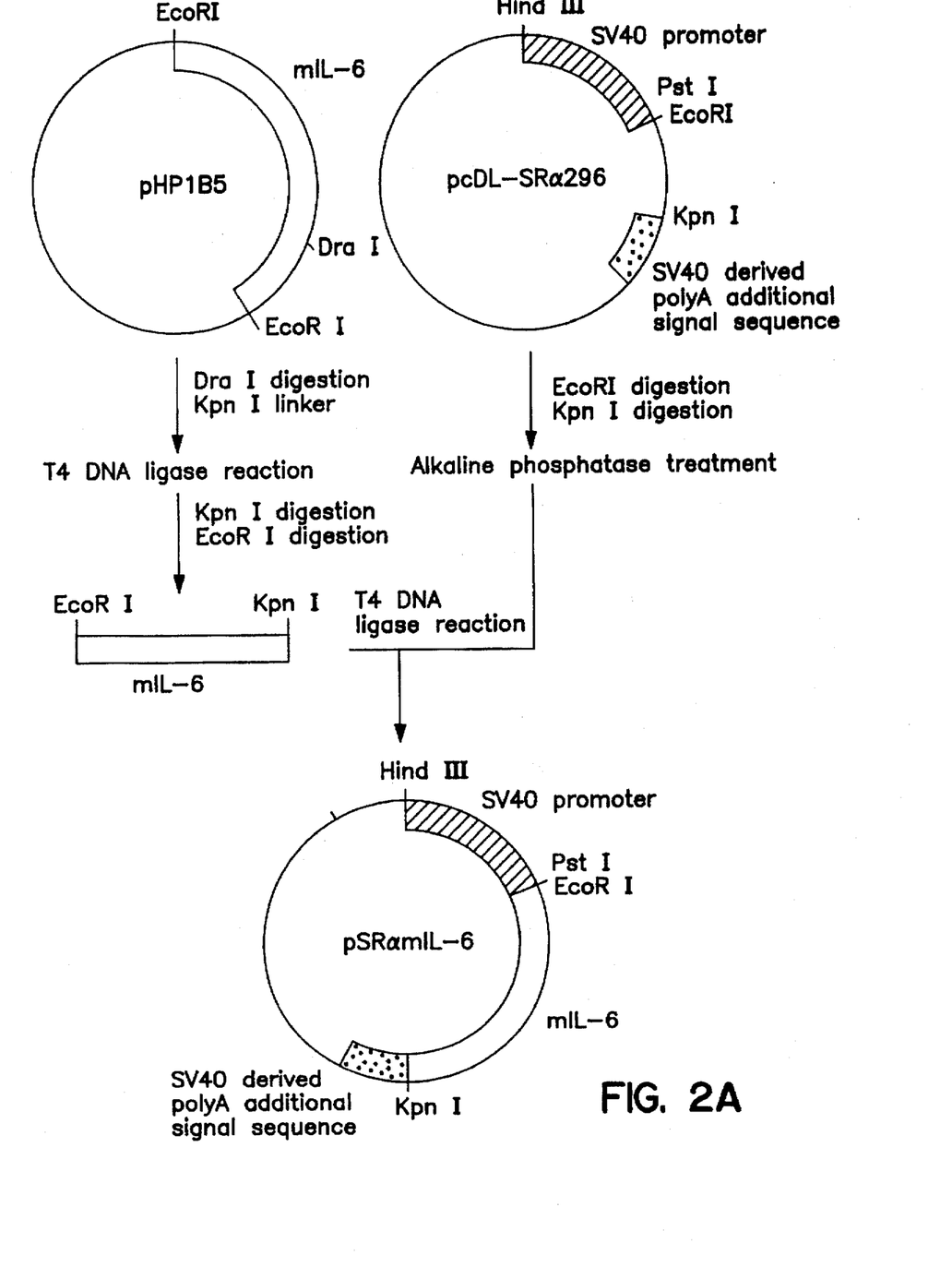
Figure 2B:
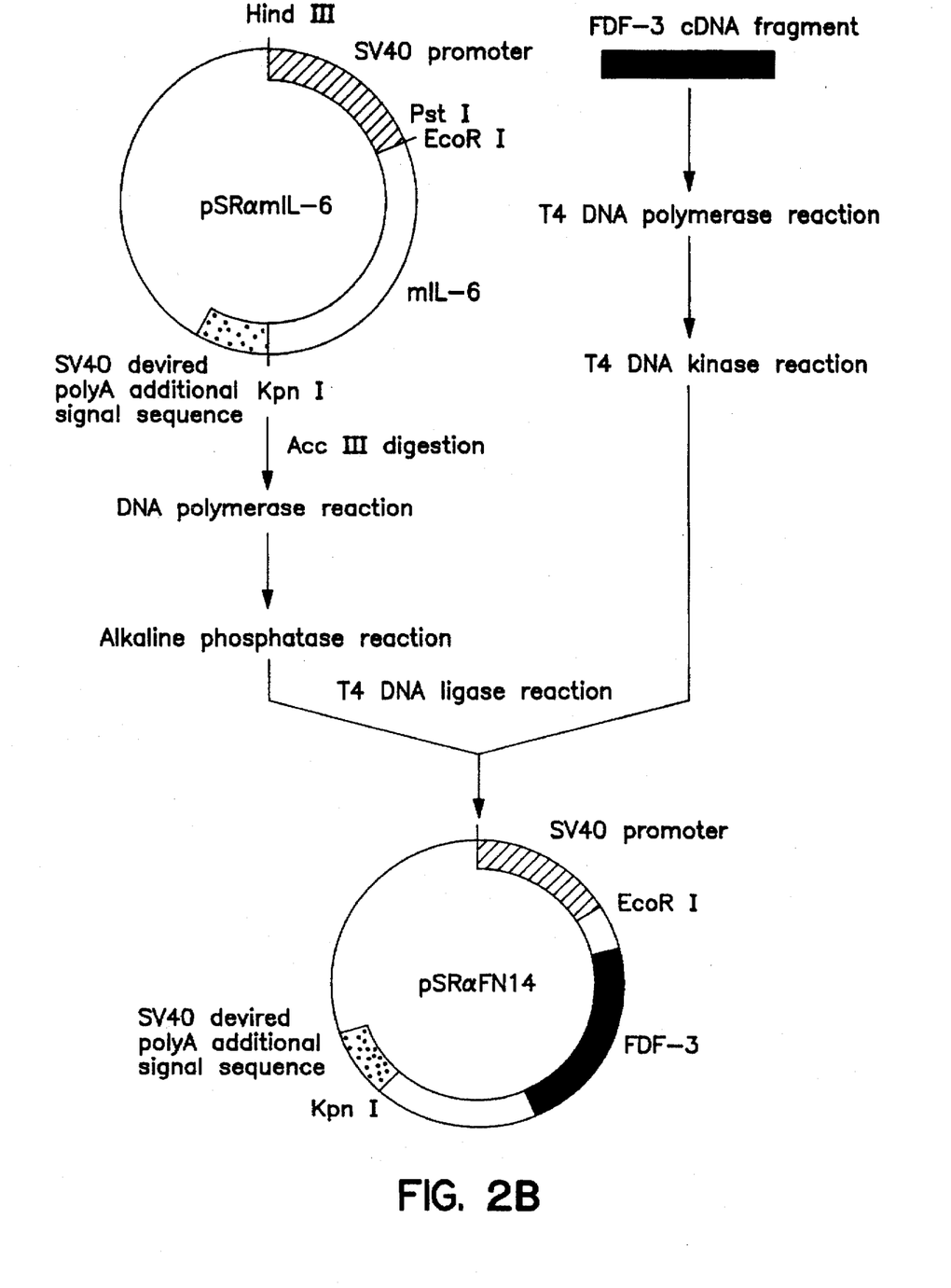

The construction of an expression vector pSRαFN14 is shown in FIGS. 2-1 and 2-2. An expression vector pcDL-SRα296 [Takebe, Y., et al., Mol. Cell. Biol. 8, 446 (1988)] was digested with restriction enzymes EcoRI and KpnI and was dephosphorytated with an alkaline phosphatase. On the other hand, a vector pHP1B5 contained with a murine IL-6cDNA [Van Snick, J., et al., Eur. J. Immunol., 18, 193 (1988)] was digested with DraI and a KpnI linker was herein ligated using T4DNA ligase. In addition, after this product was digested with EcoRI and KpnI, the DNA fragment of 830 bp containing murine IL-6 cDNA was purified by 1% agarose gel electrophoresis by a conventional method. This DNA fragment was ligated to the previously prepared pcDL-SRα296 by using T4DNA ligase. Escherichia coli was transformed by this product the and plasmid DNA was prepared from the resultant transformant by means of the conventional method (Molecular Cloning. Cold Spring Harbor Laboratory, New York, 1982) to obtain a mouse IL-6 expression vector pSRα mIL-6. pSRα mIL-6 was digested with a restriction enzyme AccIII and after blunt ends were made with DNA polymerase I (Klenow fragment), dephosphorylation was performed with alkaline phosphatase (said fragment was called "A"). On the other hand, the FDF-3cDNA fragment obtained by (2) was made into blunt ends with T4DNA polymerase based on the conventional method and in addition, phosphorylation was performed with T4DNA kinase. This DNA fragment was ligated to A obtained above with T4DNA ligase. Escherichia coli was transformed by this product and a plasmid DNA was prepared from the resultant transformant body by a conventional method. Then, it was confirmed by digesting this plasmid DNA with a restriction enzyme EcoRI that the aimed DNA fragment was integrated (said vector was called pSR FN14) and the nucleotide sequence of FDF-3cDNA was determined by means of the dideoxy method [Prober et al., Science, 238, 336 (1987)] by using Genesis 2,000 DNA analysis system (E. I. Du Pont De Nemours & Co., Inc.)(The nucleotide sequence from the first to the 5671h shown in the sequence number 5 in the Sequence Listing).

(4) Expression of FDF-3 in an animal cell pSRαFN14 was a vector expressing the chimeric protein of FDF-3 fused with the mouse IL-6. Seven amino acids on N-terminal (Phe Pro Thr Ser Gln Val Arg) were derived from the mouse IL-6 followed by the sequence of FDF-3. 10 µg of pSRαFN 14 were added in 4 ml medium of RPMI 1640 containing 50 mM tris hydrochloric acid buffer (pH 7.5), 400 µg/ml DEAE dextran (Pharmacia Co., Ltd.) and 100 µM chlorochin (Sigma Co., Ltd.). On the other hand, COS-1 cells (ATCC-CRL-1650) cultured in a RPMI1640 medium containing 10% fetal bovine serum (Gibuco Co., Ltd.) in 10 cm dishes until it reached 50% confluent were washed once with PBS and 4 ml of the above-mentioned DNA mixture were added and it was cultured under a condition of 5% $CO_2$ and at 37° C. After 4 hours the cells were washed with PBS and cultured in medium of 20 ml RPM11640 under a condition of 5% and at 37° C. The supernatant was collected and after ammonium sulfate was gradually added therein so as to make 80% saturation to dissolve it, it was stored overnight at 4° C. The precipitate was collected by means of centrifugation at 6,500 rpm for 20 minutes and was dissolved with 20 mM Tris hydrochloric acid buffer (pH 8.0) and dialysis was sufficiently performed with said buffer to make an ammonium sulfate concentrated solution.

SDS-polyacrylamide electrophoresis (4–20%) of 10 µl ammonium sulfate concentrated solution was performed under reducing condition. Thereafter, immobilization of proteins on a nitrocellulose membrane by electrophoretic transfer from gel was performed by Western blot technique and after blocking of the membrane was done with skim milk, FNS-12 (purchased from Takara Suzo Co., Ltd.) was added therein and incubated for 1 hour. After washing, an anti-mouse Ig antibody labeled with horseradish peroxydase was added and incubated for 1 hour and after washing, protein reacting with a monoclonal antibody was detected by means of the ECL system (purchased from Amsham Co., Ltd.). As the result, expression of FDF-3 was confirmed.

(5) Biological activity of recombinant FDF-3

As described said (4), pSRαFN14 was introduced into COS-1 cell and biological activity of FDF-3 which was a culture supernatant obtained by culturing for 4 days was measured by means of the method shown in Example 4. As COS-1 cells express simian IL-6, COS-1 cell, an anti-human IL-6 antibody was added to neutralize this activity and the activity for FDF-3 was measured. As the result, biological activity was detected in the recombinant FDF-3 as in the natural type as shown in Table 5.

TABLE 5

Growth activity of of recombinant FDF-3 to 5FU-treated murine hematopoietic stem cells

| Growth factor | Formation of colonies/5 × 10⁴ 5FU-resistant bone marrow cells | | | | | | |
|---|---|---|---|---|---|---|---|
| | CFU-G | CFU-GM | Macrophage | CFU-Meg | CFU-GMM | Blast | Total |
| No addition | 0 | 0 | 0 | 0 | 0 | 0 | 0 |
| rFDF-3 + IL-3 | 13.7 ± 1.9 | 20.3 ± 1.9 | 1.3 ± 0.9 | 7.0 ± 2.2 | 3.7 ± 1.2 | 0 | 46.0 ± 4.1 |
| rFDF-3 + IL-3 + αIL-6 | 12.3 ± 0.9 | 18.3 ± 1.7 | 2.3 ± 0.9 | 5.0 ± 3.7 | 5.7 ± 1.2 | 0.7 ± 0.5 | 44.3 ± 3.7 |
| IL-3 | 0.3 ± 0.5 | 0.3 ± 0.5 | 0.3 ± 0.5 | 0 | 0 | 0 | 1.0 ± 0 |
| IL-3 + IL-6 | 5.3 ± 0.5 | 39.3 ± 6.0 | 0 | 4.7 ± 1.2 | 2.7 ± 1.7 | 0 | 52.0 ± 3.6 |

TABLE 5-continued

Growth activity of of recombinant FDF-3 to 5FU-treated murine hematopoietic stem cells

| Growth factor | Formation of colonies/5 × 10⁴ 5FU-resistant bone marrow cells | | | | | | |
|---|---|---|---|---|---|---|---|
| | CFU-G | CFU-GM | Macrophage | CFU-Meg | CFU-GMM | Blast | Total |
| IL-3 + IL-6 + αIL-6 | 0.3 ± 0.5 | 1.7 ± 0.9 | 1.7 ± 0.5 | 0 | 0 | 0 | 3.7 ± 1.2 |
| IL-6 | 3.7 ± 0.9 | 2.3 ± 1.7 | 0 | 0.3 ± 0.5 | 0.3 ± 0.5 | 0 | 6.7 ± 2.9 |

Recombinant FDF-3: 5%, IL-3: 100 U/ml
Anti-human IL-6 antibody (αIL-6): 1%, hIL-6: 80 ng/ml Example 8

Cloning of cDNA of FDF-3 with different C-terminal amino acid sequences

Instead of the anti-sense primer in Example 7 (2), seven kinds of different anti-sense primers with sequences described below were used to determine nucleotide sequences of seven kinds of each FDF-3 cDNA with different C-terminal amino acids.

Anti-sense primers:

a: 5'TTAATTAACATTAGTGTTTGTTCT3' (Sequence number 6 in the Sequence Listing)
b: 5'TTAAACATTAGTGTTTGTTCTCTG3' (Sequence number 7 in the Sequence Listing)
c: 5'TTAATTAGTGTTTGTTCTCTGATG3' (Sequence number 8 in the Sequence Listing)
d: 5'TTAAGTGTTTGTTCTCTGATGGTA3' (Sequence number 9 in the Sequence Listing)
e: 5'TTAGTTTGTTCTCTGATGGTATCT3' (Sequence number 10 in the Sequence Listing)
f: 5'TTATGTTCTCTGATGGTATCTCTG3' (Sequence number 11 in the Sequence Listing)
g: 5'TTATCTCTGATGGTATCTCTGAGA3' (Sequence number 12 in the Sequence Listing)

Determined nucleotide sequences were the nucleotide sequence from the 1st to the 486th, the nucleotide sequence from the 1 st to the 489th, the nucleotide sequence from the 1st to the 492nd, the nucleotide sequence from the 1st to the 495th, the nucleotide sequence from the 1st to the 498th, the nucleotide sequence from the 1st to the 501st and the nucleotide sequence from the 1st to the 504th shown in the sequence number 5 in the sequence listing respectively.

Industrial Applicability

As the physiologically active protein of the present invention supports proliferation of the hematopoietic stem cells in the evaluation system using the murine bone marrow cells, as a stem cell growth agent wherein the physiologically active protein of the present invention is an active ingredient, it can be applied for the use of curing for suppression of the bone marrow (for example, after using an anticancer drug and bone marrow transplantation), and for bone marrow malfunction (for example, aplastic anemia etc.,) or it can be applied for the use of curing for bone marrow transplantation as an in vitro growth agent for the peripheral blood stem cells and the bone marrow stem cells. In addition, the physiologically active protein of the present invention can be used as a platelet growth agent as it stimulates megakaryocyte colonies and as a curing agent for leukopenia as it increases neutrophils.

We claim:

1. A therapeutic composition comprising:
   an FDF-3 polypeptide having a molecular weight of 18±2 kDa as determined by SDS-PAGE and having an amino acid sequence which comprises residues 1–162 as set forth in SEQ ID NO: 14; and
   a cytokine selected from the group consisting of IL-3, G-CSF, GM-CSF, and stem cell factor.

2. A composition according to claim 1, wherein the FDF-3 polypeptide has the amino acid sequence shown as residues 1–162 of SEQ ID NO: 14.

3. A composition according to claim 1, wherein the FDF-3 polypeptide has the amino acid sequence shown as residues 1–163 of SEQ ID NO: 14.

4. A composition according to claim 1, wherein the FDF-3 polypeptide has the amino acid sequence shown as residues 1–164 of SEQ ID NO: 14.

5. A composition according to claim 1, wherein the FDF-3 polypeptide has the amino acid sequence shown as residues 1–165 of SEQ ID NO: 14.

6. A composition according to claim 1, wherein the FDF-3 polypeptide has the amino acid sequence shown as residues 1–166 of SEQ ID NO: 14.

7. A composition according to claim 1, wherein the FDF-3 polypeptide has the amino acid shown as residues 1–167 of SEQ ID NO: 14.

8. A composition according to claim 1, wherein the FDF-3 polypeptide has the amino acid sequence shown as residues 1–168 of SEQ ID NO: 14.

9. A composition according to claim 1, wherein the FDF-3 polypeptide has the amino acid sequence shown as residues 1–188 of SEQ ID NO: 14.

10. A method for promoting the growth and differentiation of hematopoietic progenitor cells, comprising the step of contacting a population of progenitor cells with a composition according to any one of claims 1–9.

11. A method according to claim 10, wherein said progenitor cells are present in a patient and the method comprises the step of administering said composition to said patient.

* * * * *

UNITED STATES PATENT AND TRADEMARK OFFICE
CERTIFICATE OF CORRECTION

PATENT NO. : 5,668,104
DATED : September 16, 1997
INVENTOR(S) : Nakahata et al.

It is certified that error appears in the above-indentified patent and that said Letters Patent is hereby corrected as shown below:

Col. 22, line 41 (claim 7), insert --sequence-- after "acid."

Signed and Sealed this

Twenty-ninth Day of June, 1999

*Attest:*

Q. TODD DICKINSON

*Attesting Officer*   Acting Commissioner of Patents and Trademarks